United States Patent
Oohashi et al.

(10) Patent No.: US 11,501,751 B2
(45) Date of Patent: Nov. 15, 2022

(54) MOBILE TERMINAL WITH HIGH FREQUENCY GENERATOR

(71) Applicant: ACTION RESEARCH CO., LTD., Tokyo (JP)

(72) Inventors: Tsutomu Oohashi, Tokyo (JP); Norie Kawai, Tokyo (JP); Emi Nishina, Tokyo (JP); Manabu Honda, Tokyo (JP)

(73) Assignee: ACTION RESEARCH CO., LTD., Tokyo (JP)

( * ) Notice: Subject to any disclaimer, the term of this patent is extended or adjusted under 35 U.S.C. 154(b) by 0 days.

(21) Appl. No.: 17/210,172

(22) Filed: Mar. 23, 2021

(65) Prior Publication Data
US 2021/0210066 A1    Jul. 8, 2021

Related U.S. Application Data

(63) Continuation of application No. PCT/JP2018/036866, filed on Oct. 2, 2018.

(51) Int. Cl.
*G10K 15/04* (2006.01)
*H04R 1/02* (2006.01)
*H04R 3/04* (2006.01)
*H04W 88/02* (2009.01)

(52) U.S. Cl.
CPC ............. *G10K 15/04* (2013.01); *H04R 1/02* (2013.01); *H04R 3/04* (2013.01); *H04R 2499/11* (2013.01); *H04W 88/02* (2013.01)

(58) Field of Classification Search
CPC . G10K 15/04; H04R 1/02; H04R 3/04; H04R 2499/11; H04W 88/02
USPC .......................................................... 381/98
See application file for complete search history.

(56) References Cited

U.S. PATENT DOCUMENTS

| | | | |
|---|---|---|---|
| 2011/0152729 A1* | 6/2011 | Oohashi | A61M 21/02 601/2 |
| 2015/0086055 A1 | 3/2015 | Kato | |
| 2015/0216762 A1* | 8/2015 | Oohashi | A61M 21/02 601/47 |

FOREIGN PATENT DOCUMENTS

| | | |
|---|---|---|
| EP | 2886149 A1 | 6/2015 |
| JP | H09-313610 A | 12/1997 |
| JP | 2003-223174 A | 8/2003 |
| JP | 2005-111261 A | 4/2005 |

(Continued)

OTHER PUBLICATIONS

Japanese Office Action dated Jun. 26, 2020, with English translation, 9 pages.

(Continued)

*Primary Examiner* — Vivian C Chin
*Assistant Examiner* — Douglas J Suthers
(74) *Attorney, Agent, or Firm* — Rankin, Hill & Clark LLP

(57) ABSTRACT

To alleviate information-dependent behavior by using a mobile terminal of a user of the mobile terminal. A mobile terminal including a first signal generator that generates a frequency signal in the audible band, a second signal generator that generates a high-frequency signal in a frequency band higher than the audible band, a speaker that converts the high-frequency signal into a corresponding high-frequency sound, and a timing controller that controls timing of the generation of the high-frequency signal to be a timing that does not correlate with the timing of the generation of the frequency signal in the audible band is provided.

16 Claims, 3 Drawing Sheets

(56) References Cited

FOREIGN PATENT DOCUMENTS

| | | |
|---|---|---|
| JP | 2013-247620 A | 12/2013 |
| JP | 2015-157118 A | 9/2015 |

OTHER PUBLICATIONS

International Search Report and Written Opinion, English translations included, PCT/JP2018/036866, dated Jan. 8, 2019, 18 pages.

* cited by examiner

MOBILE TERMINAL WITH HIGH FREQUENCY GENERATOR

CROSS-REFERENCE TO RELATED APPLICATIONS

The present application is a continuation application of International Application number PCT/JP2018/036866, filed on Oct. 2, 2018. The contents of this application are incorporated herein by reference in their entirety.

BACKGROUND OF THE DISCLOSURE

Conventionally, the hypersonic effect is known to increase blood flow and activity in the deep structures of the brain, including the thalamus, hypothalamus, and midbrain (hereinafter referred to as "fundamental brain") by applying non-steady sound in a frequency band beyond the audible frequency band to humans, leading to increased immune activity, activation of reward circuitry, and stress relief (see, for example, Japanese Unexamined Patent Application Publication No. H9-313610, Japanese Unexamined Patent Application Publication No. 2003-223174, and Japanese Unexamined Patent Application Publication No. 2005-111261).

On the other hand, various types of dependencies have become a major social problem in modern society. Dependencies are conditions in which a person becomes highly dependent on stimuli in various types of information and substances that excite the reward circuitry that generates pleasure in the brain, such as alcohol, drugs, games, smartphones, gambling, and the like, which leads to consequences that hinder daily life. Since the reward circuitry controls behavior more strongly than punishment circuitry that causes discomfort and distress, it is extremely difficult to treat dependence with legal or social penalties. In particular, with the recent spread of the Internet and mobile terminals, behavior depending on information and the like obtained by operating the mobile terminal all the time has developed into new social problems such as Internet addiction disorder, gaming disorder, smartphone addiction, and the like.

BRIEF SUMMARY OF THE DISCLOSURE

The present disclosure focuses on these points, and an object of the present disclosure is to alleviate information-dependent behavior of a mobile terminal user using a mobile terminal.

The first aspect of the present disclosure provides a mobile terminal that includes a first signal generator that generates a frequency signal in the audible band, a second signal generator that generates a high-frequency signal in a frequency band higher than the audible band, a speaker that converts the high-frequency signal into a corresponding high-frequency sound, and a timing controller that controls timing of the generation of the high-frequency signal to be a timing that does not correlate with the timing of the generation of the frequency signal in the audible band.

The second aspect of the present disclosure provides a non-transitory computer readable recording medium storing a program installed in the mobile terminal provided with the speaker for converting the high-frequency sound corresponding to the high-frequency signal in the frequency band higher than the audible band, the program causing a computer to function as parts of the mobile terminal according to claim 1, when executed by the computer.

DETAILED DESCRIPTION OF THE DISCLOSURE

Hereinafter, the present invention will be described through exemplary embodiments of the present invention, but the following exemplary embodiments do not limit the invention according to the claims, and not all of the combinations of features described in the exemplary embodiments are necessarily essential to the solution means of the invention.

A Configuration Example of a Mobile Terminal 100

Figure 1:
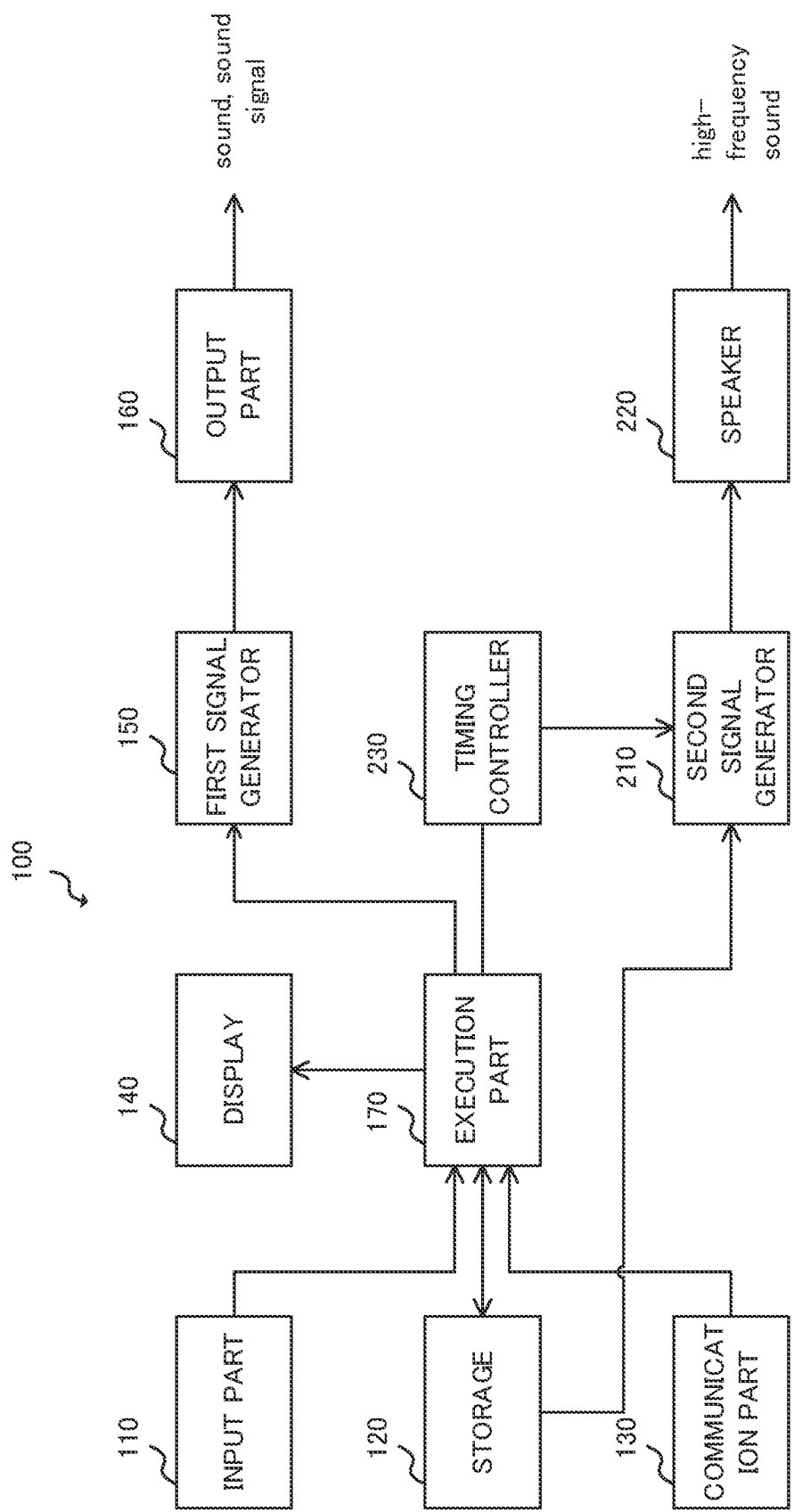
FIG. 1 shows a configuration example of a mobile terminal 100 according to the embodiment.

FIG. 1 shows a configuration example of a mobile terminal 100 according to the embodiment. The mobile terminal 100 adjusts timing for generating a high-frequency signal with a frequency higher than the audible band to alleviate information-dependent behavior of a user continuously operating the mobile terminal 100. The mobile terminal 100 is a mobile communication device, a mobile information terminal, or the like configured to be connected to a network and the like, and can acquire information, data, and the like from the outside.

The mobile terminal 100 is, for example, a device such as a mobile phone, a smart phone, a game machine, a tablet PC, a small PC, a notebook PC, or the like. The mobile terminal 100 includes an input part 110, a storage 120, a communication part 130, a display 140, a first signal generator 150, an output part 160, an execution part 170, a second signal generator 210, a speaker 220, and a timing controller 230.

The input part 110 receives an operation from a user or the like of the mobile terminal 100. The input part 110 receives, for example, an operation such as execution of application software installed in the mobile terminal 100, access to an external database and the like via a network, and execution of external software. The input part 110 includes an input device such as a touch panel, a voice input device, a gesture input device, a mouse, and a keyboard, and functions as a user interface for receiving an input from a user or the like.

The storage 120 stores an operating system (OS) and application software in which the mobile terminal 100 functions as a terminal. Further, the storage 120 may also store various types of information including a database that is referenced when the application software is being executed. The storage 120 includes, for example, a Read Only Memory (ROM) for storing a Basic Input Output System (BIOS) of a computer and the like, and a Random Access Memory (RAM) as a work area. Furthermore, the storage 120 may also include a mass storage device such as a Hard Disk Drive (HDD) and/or a Solid State Drive (SSD).

The storage 120 stores sound data for generating sound as the software is executed. Further, the storage 120 also stores high-frequency sound data for generating a high-frequency signal in a frequency band higher than the audible band. Furthermore, the storage 120 may store information such as a setting value of the mobile terminal 100. In addition, the storage 120 may store intermediate data, a calculation result, a threshold, a parameter, and the like, which are generated (or used) in the course of the operation of the mobile terminal 100. Moreover, in response to a request from each unit in the mobile terminal 100, the storage 120 may provide stored data to the requester.

The communication part 130 communicates with the outside of the mobile terminal 100. For example, the communication part 130 connects to the network wirelessly or by wire to transmit and receive data to and from an external database and the like. The communication part 130 may be connected to a telephone line and the like for communication. The communication part 130 illustratively includes an antenna, a network I/O device, and the like.

The display 140 displays an image and the like in response to the execution of the application software, the OS, the utility software, and the like. The display 140 includes a display panel and the like, and displays numeric data, character information, a still image, a video, an operating state or communication state of the software or the mobile terminal 100, a web page being browsed, and the like.

The first signal generator 150 generates a frequency signal in the audible band. The first signal generator 150 generates, for example, an electrical signal for playing sound corresponding to the sound data as a frequency signal. For example, the first signal generator 150 generates a frequency signal in a band from about 20 Hz to about 20 kHz. The first signal generator 150 provides the generated frequency signal to the output part 160.

The output part 160 provides the frequency signal to the outside. The output part 160 includes, for example, a PHONE plug, an RCA plug, an optical digital terminal, a coaxial digital terminal, an HDMI (registered trademark) terminal, and the like. Further, the output part 160 may have a speaker that converts the frequency signal into sound in the audible band.

The execution part 170 controls the operation of the mobile terminal 100. The execution part 170 is, for example, a Central Processing Unit (CPU), and acquires a user's instruction through the input part 110 and executes the application software according to the instruction. The execution part 170 may execute a program and the like in the mobile terminal 100 at a predetermined timing or the like. The execution part 170 starts executing the OS when the mobile terminal 100 is activated, for example.

Further, the execution part 170 reads the software and the like to be executed from the storage 120. The execution part 170 may store intermediate data, an execution result, and the like of the software in the storage 120. The execution part 170 may acquire information and the like of the software to be executed via the communication part 130. Furthermore, the execution part 170 displays information and the like associated with the execution of the software on the display 140. In addition, the execution part 170 provides the first signal generator 150 with the sound data associated with the execution of the software to cause an internal speaker, external speaker, or the like to generate the sound.

The above-mentioned mobile terminal 100 can execute a game, play a video, play sound, browse web information, and the like according to the user's operation. The user desirably uses the mobile terminal 100 as necessary or as entertainment, only for an appropriate period of time. However, a user under stress or the like sometimes uses the mobile terminal 100 as a means of escape and the like. In this case, the escape time may continue depending on the degree of stress or the like, and so the user sometimes falls into information-dependent behavior, such as gaming disorder, gambling disorder, and dependence on the mobile terminal 100 itself, in which the user operates the mobile terminal 100 all the time.

Therefore, the mobile terminal 100 according to the embodiment includes a second signal generator 210, a speaker 220, and a timing controller 230 to reduce such information-dependence of the user.

The second signal generator 210 generates a high-frequency signal in a frequency band higher than the audible band. The second signal generator 210 generates, for example, a high-frequency signal in a frequency band higher than about 20 kHz. The second signal generator 210 reads, for example, high-frequency sound data stored in the storage 120, and generates a high-frequency signal corresponding to the high-frequency sound data. The second signal generator 210 supplies the generated high-frequency signal of electrical signal to the speaker 220.

The speaker 220 converts the high-frequency signal received from the second signal generator 210 into a corresponding high-frequency sound. The speaker 220 is preferably provided so as to be close to a user who is using the mobile terminal 100. That is, the speaker 220 is preferably provided within a range in which the high-frequency sound is transmitted to the brain of the user through at least a part of the user's body. The speaker 220 is preferably provided on an externally facing surface such as the front, back, and sides of the mobile terminal 100. The speaker 220 is, for example, a piezoelectric actuator.

The timing controller 230 controls the timing for the second signal generator 210 generating the high-frequency signal. That is, the timing controller 230 controls the timing for the mobile terminal 100 outputting the high-frequency sound. The timing controller 230 controls the timing of the generation of the high-frequency signal to be a timing that does not correlate with the timing at which the first signal generator 150 generates the frequency signal in the audible band. That is, the timing controller 230 controls the second signal generator 210 to cause the mobile terminal 100 to output the high-frequency sound regardless of the timing of outputting an audible sound from the output part 160.

It should be noted that the timing controller 230 may acquire information about the state of the execution part 170 executing application software and the like from said execution part 170. Further, the CPU functioning as the execution part 170 may constitute the timing controller 230, or a CPU or an electric circuit that is different from the CPU functioning as the execution part 170 may constitute the timing controller 230.

As described above, the mobile terminal 100 according to the embodiment applies the high-frequency sound to the user at the timing that is different from that of the sound signal and the sound generated by the application software executed by the user. For example, the timing controller 230, in a state where the mobile terminal 100 is turned on, controls the second signal generator 210 so as to cause the second signal generator 210 to generate the high-frequency signal. In this manner, the mobile terminal 100 keeps applying the high-frequency sound while the user is using the mobile terminal 100.

Although humans cannot directly hear sounds in a frequency band beyond the audible frequency band, it is known that, when they are propagated to the brain, they have the effect of increasing cerebral blood flow of the reward circuitry to relieve stress, thereby relaxing humans (hypersonic effect). Therefore, even if the user operates the mobile terminal 100 in a stressful state or in a condition where the user has accumulated stress, the mobile terminal 100 can alleviate the user's stress and cause the user to relax. Since the mobile terminal 100 applies the high-frequency sound every time the user uses the mobile terminal 100, stress can be relieved in the course of the user's daily life, thereby improving the mental and physical condition of the user.

Here, it is considered that humans receive the high-frequency sound via a body surface. The mobile terminal 100 according to the embodiment includes the speaker 220 for outputting the high-frequency sound on at least one of the front surface, the back surface, the side surface, and the like, and outputs the high-frequency sound to the user's body surface. This enables to propagate the high-frequency sound into the user's body when the user holds the mobile terminal 100 by hand and puts the mobile terminal 100 in a pocket or the like. In addition, since the high-frequency sound is not a sound propagated to the brain through a tympanic membrane of humans, the mobile terminal 100 can provide the hypersonic effect to the user even if the user listens to music using an earphone or the like.

It should be noted that the mental and physical state of the user may be relatively light stress and the like that does not hinder daily life, or may be severe stress and the like that requires treatment at a medical institution or the like. If a person feels sever stress or the like, the person sometimes operates the mobile terminal for a longer time than necessary. The user sometimes falls into dependent behavior in which, for example, the user who does not usually enjoy games spends a long time playing a game when he/she feels stress.

Further, the user sometimes becomes highly dependent on stimuli in various types of information and substances that excite the reward circuitry that generates pleasure in the user's brain, such as alcohol, drugs, games, smartphones, gambling, and the like, which leads to consequences that hinder daily life. Since the reward circuitry controls the behavior more strongly than the punishment circuitry that causes discomfort and distress, it is extremely difficult to treat dependence with legal or social penalties. In particular, with the recent spread of the Internet and mobile terminals, behavior depending on information and the like obtained by operating the mobile terminal all the time has developed into new social problems such as Internet addiction disorder, gaming disorder, smartphone addiction, and the like.

One approach for avoiding such dependence is "replacement therapy." Replacement therapy is generally therapy in which a chemical or the like, which is less harmful compared with dependent behavior that physically harms the user, is administered as a substitute for activating the reward circuitry that causes the dependence, and then the dosage is gradually decreased to have the person get better. Such replacement therapy has been shown to be effective in dependent behavior such as alcoholism, nicotine dependence, substance dependence, and the like. Since the mobile terminal 100 according to the embodiment applies the high-frequency sound, which is information less harmful than such a chemical substance and the like used in replacement therapy, to the user, it can be used while reducing the risk caused by the administration of such chemicals. In addition, since the high-frequency sound can be applied regardless of the age and the like of the user, the hypersonic effect can substitute for the activation of the reward circuitry even for, for example, information-dependence and the like of a person who is under age.

An Example of Controlling the Timing for Generating the High-Frequency Sound

It should be noted that, in order to cope with various states of the users, it is desirable that the timing for the mobile terminal 100 generating the high-frequency signal can be adjusted according to the state of the user. For example, the mobile terminal 100 can determine the state of the user on the basis of the state of the application being executed by the user. Therefore, the timing controller 230 controls the timing for generating the high-frequency signal on the basis of the state of the execution part 170 executing the application software.

For example, the timing controller 230 controls the timing for generating the high-frequency signal on the basis of a period of time during which the execution part 170 is continuously executing the application software. For example, the timing controller 230 stops generating the high-frequency signal at a time when the period of time during which the execution part 170 has been continuously executing the application software exceeds a threshold.

Thus, when the user executes the application software, the mobile terminal 100 relieves the stress of the user until the predetermined period of time has passed. The mobile terminal 100 then stops applying the high-frequency sound after the predetermined period of time has passed, and the user exits the state of comfort thereby prompting the user to stop executing the game software. Therefore, the mobile terminal 100 can alleviate the dependence of the user that causes, for example, the user to play games and browse websites for a long time. In addition, by setting the threshold of the duration according to the user's dependence state, the degree of effect of continuously relaxing the dependence state can be adjusted.

In addition, the timing controller 230 determines whether or not to control the timing for generating the high-frequency signal on the basis of the type of application software being executed by the execution part 170. For example, the timing controller 230 stops generating the high-frequency signal when a user has been playing with game software. When the user executes application software other than the game software, the mobile terminal 100 relieves the stress of the user. If the user executes the game software, the mobile terminal stops applying the high-frequency sound, and the user exits the state of comfort thereby prompting the user to stop executing the game software.

<A Negative Band>

It should be noted that, an example in which the high-frequency sound is in the frequency band higher than the frequency of about 20 kHz in the mobile terminal 100 according to the embodiment has been described. Such a high-frequency sound includes a band which exerts the hypersonic effect on a human, but also includes a component in a band which exerts an effect different from the hypersonic effect. For example, frequency components from approximately 16 kHz to approximately 32 kHz are known to reduce the activity of nuclei of humans, as opposed to the hypersonic effect. In the embodiment, the frequency band from approximately 16 kHz to approximately 32 kHz is referred to as a negative band.

Further, it is also known that frequency components from approximately 32 kHz to approximately 40 kHz have almost nothing to do with the hypersonic effect. Furthermore, it is known that frequency components of approximately 40 kHz or more are in a band which exerts the hypersonic effect on humans. It should be noted that the upper limit frequency of the band for exerting the hypersonic effect is not yet understood, but may be approximately 150 kHz, approximately 200 kHz, or the like.

As described above, even a sound in the frequency band higher than the audible band may generate an effect opposite to the hypersonic effect like the negative band. Therefore, the mobile terminal 100 according to the embodiment may further include a filter for removing the sound signal in the negative band. For example, the second signal generator 210 has a filter part for passing frequency components in a predetermined frequency band of the high-frequency signal, and outputs frequency components passed through the filter part as the high-frequency signal. In this case, the frequency components passed through the filter part are components having a frequency higher than approximately 32 kHz. The filter part may be a high-pass filter, a band-pass filter, a band-rejection filter, or the like, or combinations thereof.

An example in which the mobile terminal 100 according to the embodiment applies the high-frequency sound for generating the hypersonic effect to the user has been described above, but the present disclosure is not limited thereto. The mobile terminal 100 may apply the high-frequency sound in the negative band to the user. Such a mobile terminal 100 will be described below.

Figure 2:
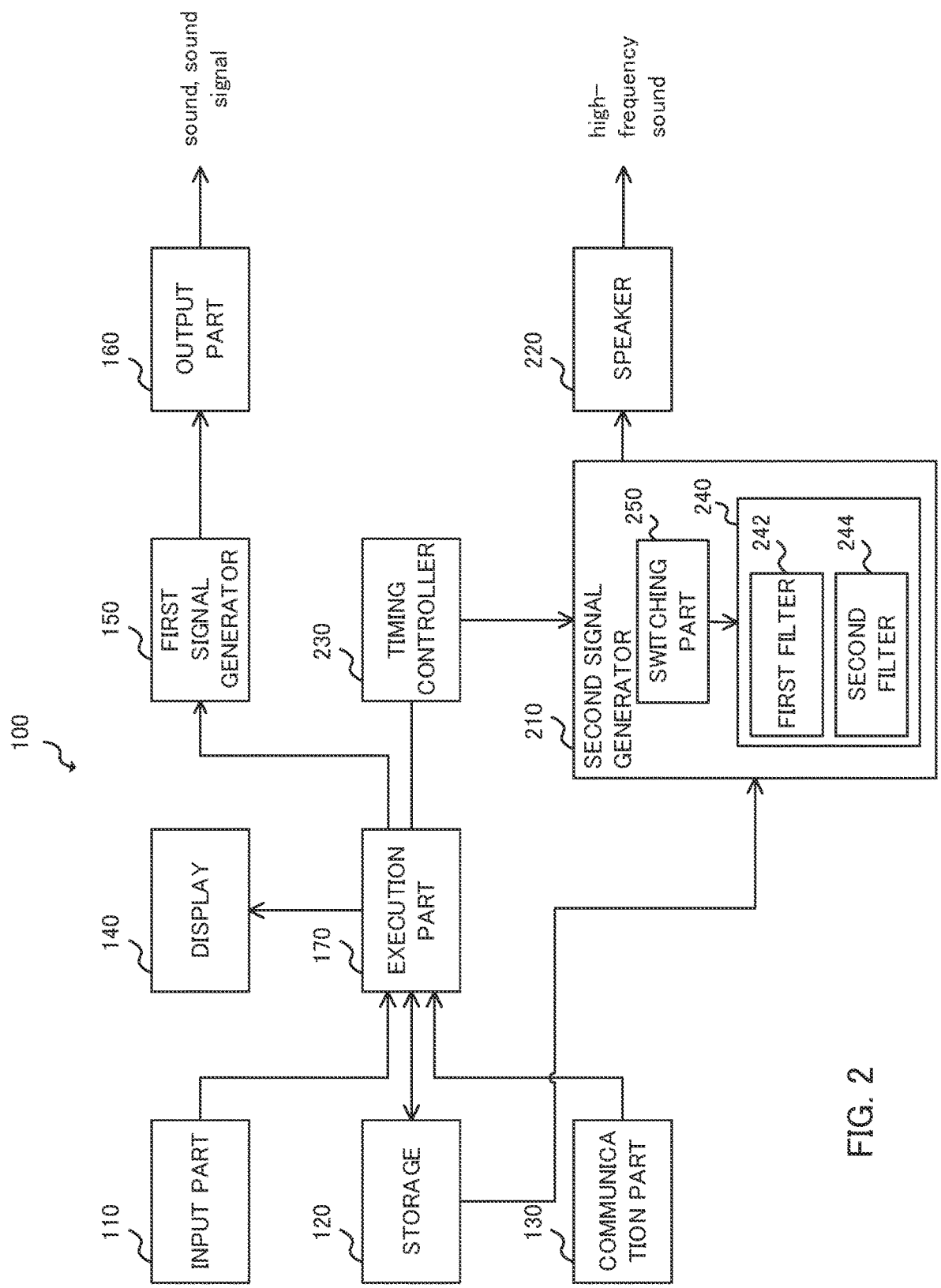
FIG. 2 shows a first variation of the mobile terminal 100 according to the embodiment.

An Example of Controlling the Timing for Generating the High-Frequency Sound in the Negative Band FIG. 2 shows the first variation of the mobile terminal 100 according to the embodiment. The mobile terminal 100 of the first variation switches the frequency band of the high-frequency sound to be applied to the user. In the mobile terminal 100 of the first variation shown in FIG. 2, the operation substantially the same as that of the mobile terminal 100 shown in FIG. 1 is denoted by the same reference numeral, and description thereof is omitted. In the mobile terminal 100 of the first variation, the second signal generator 210 includes a filter part 240 and a switching part 250.

The filter part 240 includes a first filter 242 for passing the frequency components of 32 kHz or less of the high-frequency signal. That is, the first filter 242 passes the high-frequency signal in the negative band and reduces the components of the frequency higher than approximately 32 kHz. Further, the filter part 240 has a second filter 244 for passing the components of the frequency higher than 32 kHz of the high-frequency signal. That is, the second filter 244 reduces the high-frequency signal in the negative band and passes the components of the frequency higher than approximately 32 kHz. The first filter 242 and the second filter 244 each may be a high-pass filter, a low-pass filter, a band-pass filter, a band-rejection filter, or the like, or combinations thereof.

The switching part 250 switches to either one of the first filter 242 and the second filter 244 as the filter used by the filter part 240. That is, if the switching part 250 switches to the first filter 242, the second signal generator 210 supplies the high-frequency signal having a frequency band of approximately 32 kHz or less to the speaker 220. Further, if the switching part 250 switches to the second filter 244, the second signal generator 210 supplies the high-frequency signal having a frequency band higher than approximately 32 kHz to the speaker 220.

With respect to the second signal generator 210 having such a filter part 240, the timing controller 230 further controls whether the second signal generator 210 inputs the high-frequency signal to the first filter 242 or the second filter 244. The timing controller 230 controls the switching part 250 to switch to either one of the first filter 242 and the second filter 244 as the filter to be used by the filter part 240.

For example, the timing controller 230 switches the filter of the filter part 240 to the first filter 242 at a time when the period of time during which the user has been executing the application software exceeds the threshold. Thus, the mobile terminal 100 relieves the stress of the user until the predetermined time has passed while the user is executing the application software. The mobile terminal 100 then applies the high-frequency sound in the negative band after the predetermined period of time has elapsed, and the user exits the state of comfort thereby prompting the user to stop executing the game software.

Therefore, the mobile terminal 100 can alleviate the dependence of the user that causes, for example, the user to play games and browse websites for along time. It should be noted that the application of the negative band by the mobile terminal 100 reduces the activity of nuclei of humans, and therefore the negative band is desirable to be used for a user having a relatively light dependence. Further, it is desirable to set a duration which is a threshold according to the dependence of the user. In addition, the mobile terminal 100 may be provided with two thresholds, stop applying the high-frequency sound after the first threshold time has passed, and apply the high-frequency sound in the negative band to the user after the second threshold time has passed.

The timing controller 230 may also generate the high-frequency signal in the negative band when the user has been executing the game software. Thus, when the user executes the application software other than the game software, the mobile terminal 100 relieves the stress of the user. The mobile terminal 100 then applies the high-frequency sound in the negative band when the user executes the game software, and the user exits the state of comfort thereby prompting the user to stop executing the game software.

An example in which the above-described mobile terminal 100 according to the embodiment controls the timing for applying the high-frequency sound in the frequency band higher than at least approximately 32 kHz to the user has been described, but the present disclosure is not limited thereto. For example, the filter part 240 may have only the first filter 242, and the mobile terminal 100 may control the timing to apply the high-frequency sound in the negative band to the user, the timing to stop applying the high-frequency sound in the negative band, and the like.

An example in which the above-described mobile terminal 100 according to the embodiment applies the high-frequency sound in the frequency band higher than the audible band to the user when the mobile terminal 100 is turned on has been described, but the present disclosure is not limited thereto. Since the high-frequency sound is transmitted to the brain through at least a part of the human body, it is desirable that the mobile terminal 100 is close to the user. Further, it is more desirable that the speaker 220 of the mobile terminal 100 is in contact with the user. Therefore, the mobile terminal 100 may apply the high-frequency sound in the frequency band higher than the audible band to the user in response to the mobile terminal 100 getting close to the user. Such a mobile terminal 100 will be described below.

Figure 3:
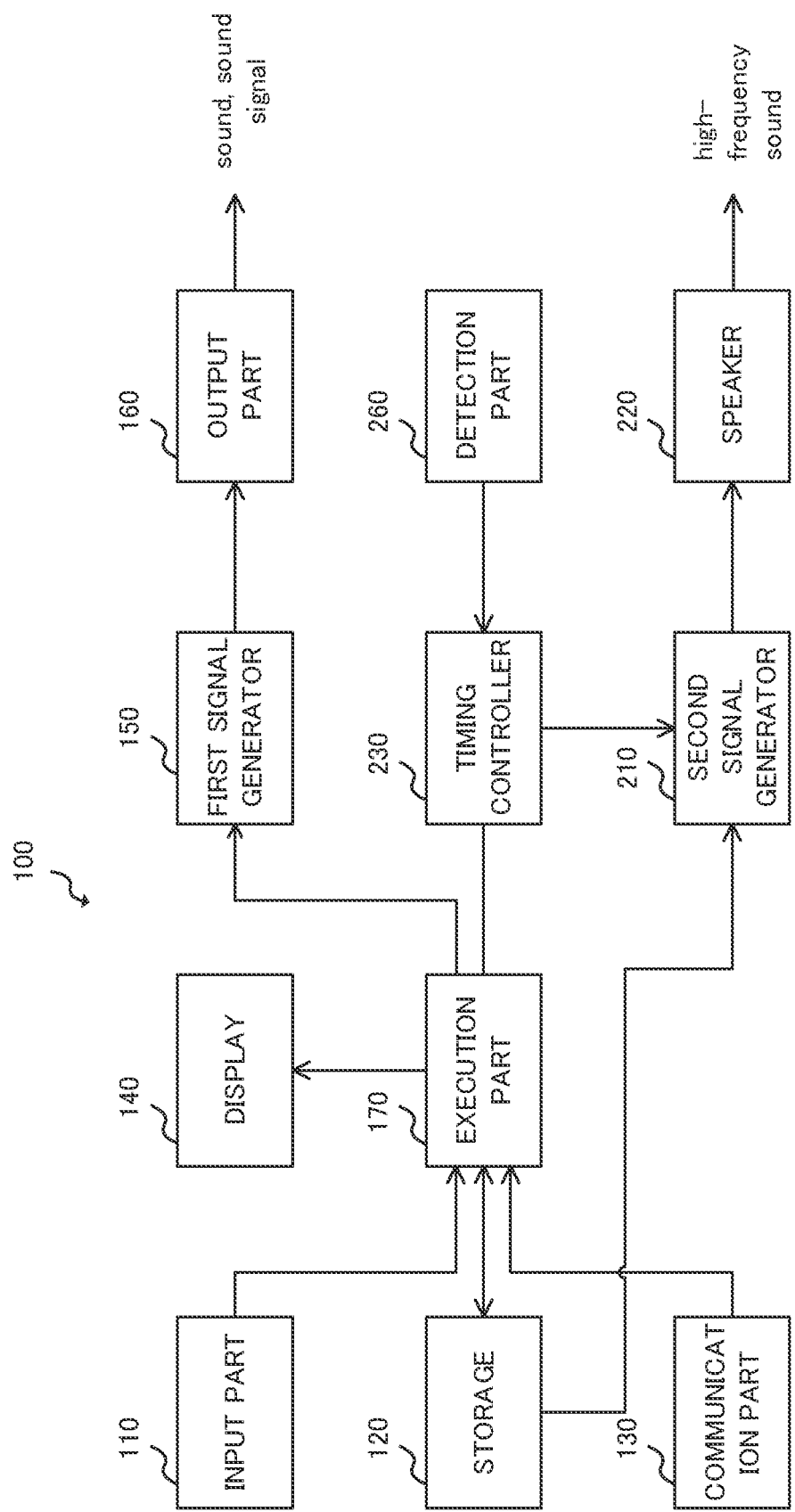
FIG. 3 shows a second variation of the mobile terminal 100 according to the embodiment.

An Example of Controlling the Timing for Generating the High-Frequency Sound if the Speaker 220 is Close to the User FIG. 3 shows the second variation of the mobile terminal 100 according to the embodiment. The mobile terminal 100 of the second variation detects whether or not the speaker 220 is close to the user, and switches the timing for generating the high-frequency sound according to the detection result. In the mobile terminal 100 of the second variation shown in FIG. 3, the operation substantially the same as that of the mobile terminal 100 shown in FIG. 1 is denoted by the same reference numeral, and description thereof is omitted. The mobile terminal 100 of the second variation further includes a detection part 260.

The detection part 260 detects whether or not the user is close to the speaker 220. For example, when the detection part 260 detects that the mobile terminal 100 is held by the user, the detection part 260 detects that the user is in close proximity. It should be noted that it is preferable that the speaker 220 is provided at a position that is close to or in contact with the user's hand when the mobile terminal 100 is held by the user.

Further, the detection part 260 may determine that the user is close to the terminal 100 when predetermined software such as game software, a browser, or the like is executed. In addition, the detection part 260 may determine that the user is close when movement, a temperature rise, or the like of the mobile terminal 100 is detected. The detection part 260 may acquire the execution status of the application software from the execution part 170, and may also include an accelerometer, a gyroscope, a global positioning system (GPS), a temperature sensor, and the like. The detection part 260 provides the detection result to the timing controller 230.

The timing controller 230 controls the timing for generating the high-frequency signal in accordance with the detection result of the detection part 260. The timing controller 230 controls and causes the second signal generator 210 to generate the high-frequency signal in response to, for example, receiving the detection result indicating that the speaker 220 and the user are close to each other. Further, the timing controller 230 may control the timing for generating the high-frequency signal in the frequency band higher than approximately 32 kHz, the high-frequency signal in the negative band, and the like, on a condition that the timing controller 230 receives the detection result indicating that the speaker 220 and the user are close to each other.

The mobile terminal 100 of the second variation described above does not generate the high-frequency sound if the high-frequency sound is unlikely to be propagated into the user's body because the speaker 220 and the user are separated from each other. As a result, the mobile terminal 100 can reduce power consumption and efficiently propagate the high-frequency sound into the user's body.

At least a part of the mobile terminal 100 according to the embodiment described above is, for example, a computer and the like. The computer and the like functions as, for example, the input part 110, the storage 120, the communication part 130, the display 140, the first signal generator 150, the output part 160, the execution part 170, the second signal generator 210, the speaker 220, the timing controller 230, and the like according to the embodiment, by executing a program or the like.

The computer includes a processor such as a central processing unit (CPU), and executes a program stored in the storage 120 to function as at least a part of the input part 110, the communication part 130, the first signal generator 150, the output part 160, the execution part 170, the second signal generator 210, the timing controller 230, the filter part 240, the switching part 250, and the detection part 260. The computer may further include a Graphics Processing Unit (GPU) and the like. It should be noted that the program is installed in, as an example, the mobile terminal 100 provided with the speaker 220 for converting the high-frequency sound corresponding into the high-frequency signal in the frequency band higher than the audible band. Further, the computer is also implemented in such a mobile terminal 100.

The present disclosure is explained on the basis of the exemplary embodiments. The technical scope of the present disclosure is not limited to the scope explained in the above embodiments and it is possible to make various changes and modifications within the scope of the disclosure. For example, the specific embodiments of the distribution and integration of the apparatus are not limited to the above embodiments, all or part thereof, can be configured with any unit which is functionally or physically dispersed or integrated. Further, new exemplary embodiments generated by arbitrary combinations of them are included in the exemplary embodiments of the present disclosure. Further, effects of the new exemplary embodiments brought by the combinations also have the effects of the original exemplary embodiments.

What is claimed is:

1. A mobile terminal comprising:
a first signal generator that generates a frequency signal in an audible band;
a second signal generator that generates a high-frequency signal in a frequency band higher than the audible band;
a speaker that converts the high-frequency signal into a corresponding high-frequency sound;
a timing controller that controls timing of the generation of the high-frequency signal to be a timing that does not correlate with a timing of the generation of the frequency signal in the audible band; and
an execution part that executes application software,
wherein the timing controller controls the timing for generating the high-frequency signal on a basis of a state where the execution part is executing application software, and
wherein the timing controller controls the timing for generating the high-frequency signal on the basis of a period of time during which the execution part is continuously executing application software.

2. The mobile terminal according to claim 1, wherein the timing controller controls and causes the second signal generator to generate the high-frequency signal when the mobile terminal is turned on and is powered.

3. The mobile terminal according to claim 1, wherein the timing controller determines whether or not to control the timing for generating the high-frequency signal on a basis of a type of application software being executed by the execution part.

4. The mobile terminal according to claim 1, wherein the timing controller stops generating the high-frequency signal at a time when the a period of time during which the execution part has been continuously executing application software exceeds a threshold.

5. The mobile terminal according to claim 1, wherein the second signal generator has a filter part that passes frequency components in a predetermined frequency band of the high-frequency signal, and outputs the frequency components passed through the filter part as the high-frequency signal.

6. The mobile terminal according to claim 5, wherein the filter part has a first filter for passing the frequency components of 32 kHz or less of the high-frequency signal.

7. The mobile terminal according to claim 5, wherein
the filter part includes a second filter for passing the frequency components higher than 32 kHz of the high-frequency signal.

8. The mobile terminal according to claim 5, wherein
the filter part includes a first filter for passing the frequency components of 32 kHz or less of the high-frequency signal, and a second filter for passing the frequency components higher than 32 kHz of the high-frequency signal, and
the timing controller further controls whether the second signal generator inputs the high-frequency signal to the first filter or the second filter.

9. The mobile terminal according to claim 8, further comprising:
an execution part that executes application software, wherein
the timing controller outputs the frequency components passed through a first filter part as the high-frequency signal at a time when a period of time during which the execution part has been continuously executing application software exceeds a threshold.

10. The mobile terminal according to claim 1, further comprising:
a detection part that detects whether or not a user is close to the speaker, wherein
the timing controller controls the timing for generating the high-frequency signal in accordance with a detection result of the detection part.

11. The mobile terminal according to claim 10, wherein
the detection part detects that the user is close to the speaker when the detection part detects that the mobile terminal is held by the user.

12. A non-transitory computer readable recording medium storing a program causing a computer to function as the mobile terminal of claim 1, the program installed in the mobile terminal provided with the speaker for converting the high-frequency sound corresponding to the high-frequency signal in the frequency band higher than the audible band, when executed by the computer.

13. A mobile terminal comprising:
a first signal generator that generates a frequency signal in an audible band;
a second signal generator that generates a high-frequency signal in a frequency band higher than the audible band;
a speaker that converts the high-frequency signal into a corresponding high-frequency sound; and
a timing controller that controls timing of the generation of the high-frequency signal to be a timing that does not correlate with a timing of the generation of the frequency signal in the audible band,
wherein the second signal generator has a filter part that passes frequency components in a predetermined frequency band of the high-frequency signal, and outputs the frequency components passed through the filter part as the high-frequency signal, and
wherein the filter part has a first filter for passing the frequency components of 32 kHz or less of the high-frequency signal.

14. The mobile terminal according to claim 13, wherein
the filter part includes a second filter for passing the frequency components higher than 32 kHz of the high-frequency signal.

15. The mobile terminal according to claim 13, wherein
the filter part includes a first filter for passing the frequency components of 32 kHz or less of the high-frequency signal, and a second filter for passing the frequency components higher than 32 kHz of the high-frequency signal, and
the timing controller further controls whether the second signal generator inputs the high-frequency signal to the first filter or the second filter.

16. The mobile terminal according to claim 15, further comprising:
an execution part that executes application software, wherein
the timing controller outputs the frequency components passed through a first filter part as the high-frequency signal at a time when a period of time during which the execution part has been continuously executing application software exceeds a threshold.

* * * * *